US009883918B2

(12) United States Patent
Chmiel et al.

(10) Patent No.: US 9,883,918 B2
(45) Date of Patent: Feb. 6, 2018

(54) METHOD FOR MAPPING VENTRICULAR/ATRIAL PREMATURE BEATS DURING SINUS RHYTHM

(71) Applicant: BIOSENSE WEBSTER (ISRAEL) LTD., Yokneam (IL)

(72) Inventors: Yoram Chmiel, Kefar Yona (IL); Gal Hayam, Tivon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/465,316

(22) Filed: Mar. 21, 2017

(65) Prior Publication Data
US 2017/0189134 A1   Jul. 6, 2017

Related U.S. Application Data

(62) Division of application No. 14/024,859, filed on Sep. 12, 2013, now Pat. No. 9,642,674.

(51) Int. Cl.
*A61B 5/0464* (2006.01)
*A61B 18/14* (2006.01)
*A61B 5/00* (2006.01)
*A61B 5/044* (2006.01)
*A61B 5/042* (2006.01)
(Continued)

(52) U.S. Cl.
CPC .............. *A61B 90/37* (2016.02); *A61B 5/044* (2013.01); *A61B 5/0422* (2013.01); *A61B 5/0464* (2013.01); *A61B 5/062* (2013.01); *A61B 5/6852* (2013.01); *A61B 18/1492* (2013.01); *A61B 2017/00053* (2013.01); *A61B 2018/00351* (2013.01); *A61B 2018/00577* (2013.01);
(Continued)

(58) Field of Classification Search
CPC .............. A61B 18/1492; A61B 5/0422; A61B 2018/00642; A61B 18/00869; A61B 5/0402; A61B 5/0464; A61B 5/046; A61B 5/063; A61B 2017/00053; A61B 2018/00351; A61B 2018/00577; A61B 5/6852; A61B 5/062; A61B 90/37; A61B 5/044; A61B 2023/2051
See application file for complete search history.

(56) References Cited

U.S. PATENT DOCUMENTS 5,443,489 A    8/1995    Ben-Haim
6,226,542 B1   5/2001    Reisfeld
(Continued)

FOREIGN PATENT DOCUMENTS

EP      1420690 A1    5/2004
WO   2012092016 A1    7/2012

OTHER PUBLICATIONS

European Search Report for corresponding European patent application No. 14184393.8, dated Jan. 27, 2015.

*Primary Examiner* — Mark W Bockelman
(74) *Attorney, Agent, or Firm* — Notaro, Michalos & Zaccaria P.C.

(57) ABSTRACT

While detecting a cardiac arrhythmia, a mapping electrode of a probe is used to associate a local activation time with a first location in a region of interest in the heart. While detecting an absence of the cardiac arrhythmia, the local activation time is associated with a second location in the heart. Electrical data of the first location is assigned to the second location, and an electroanatomic map of the heart is generated that includes the second location in association with the assigned electrical data of the first location.

3 Claims, 6 Drawing Sheets

(51) Int. Cl.
  *A61B 5/06* (2006.01)
  *A61B 90/00* (2016.01)
  A61B 17/00 (2006.01)
  A61B 18/00 (2006.01)
  A61B 34/20 (2016.01)

(52) U.S. Cl.
  CPC ............... *A61B 2018/00839* (2013.01); *A61B 2034/2051* (2016.02)

(56) References Cited

U.S. PATENT DOCUMENTS

| | | |
|---|---|---|
| 6,301,496 B1 | 10/2001 | Reisfeld |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,245,962 B2 | 7/2007 | Ciaccio et al. |
| 7,536,218 B2 | 5/2009 | Govari et al. |
| 7,756,576 B2 | 7/2010 | Levin |
| 7,907,994 B2 | 3/2011 | Stolarski et al. |
| 2005/0209524 A1 | 9/2005 | Donaldson |
| 2009/0099468 A1 | 4/2009 | Thiagalingam et al. |
| 2010/0268059 A1 | 10/2010 | Ryu et al. |
| 2011/0144510 A1 | 6/2011 | Ryu et al. |

METHOD FOR MAPPING VENTRICULAR/ATRIAL PREMATURE BEATS DURING SINUS RHYTHM

CROSS REFERENCE TO RELATED APPLICATION

This is a divisional of application Ser. No. 14/024,859, filed Sep. 12, 2013 and incorporated here by reference.

BACKGROUND OF THE INVENTION

Field of the Invention

This invention relates to invasive medical devices. More particularly, this invention relates to identifying the anatomical origin of infrequent premature contractions of the heart chambers using an invasive probe.

Description of the Related Art

The meanings of certain acronyms and abbreviations used herein are given in Table 1.

TABLE 1

Acronyms and Abbreviations

| | |
|---|---|
| CL | Cycle Length |
| IS | Induced Signal |
| LAT | Local Activation Time |
| PM | Pace Mapped |
| PVC | Premature Ventricular Contraction |
| SR | Sinus Rhythm |
| VT | Ventricular Tachycardia |

Cardiac arrhythmia, such as atrial fibrillation, occurs when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local electrogram or local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector.

Mapping the activation front and conduction fields aids the physician in identifying and diagnosing abnormalities, such as ventricular and atrial tachycardia and ventricular and atrial fibrillation, which result from areas of impaired electrical propagation in the heart tissue.

Localized defects in the heart's conduction of activation signals may be identified by observing phenomena such as multiple activation fronts, abnormal concentrations of activation vectors, or changes in the velocity vector or deviation of the vector from normal values. Examples of such defects include re-entrant areas, which may be associated with signal patterns known as complex fractionated electrograms. Once a defect is located by such mapping, it may be ablated (if it is functioning abnormally) or otherwise treated to restore the normal function of the heart insofar as is possible.

Mapping of the electrical activation time in the heart muscle requires that the location of the sensor within the heart be known at the time of each measurement. In the past, such mapping was performed using a single movable electrode sensor inside the heart, which sensor measured activation time relative to a fixed external reference electrode. This technique, however, requires calibration, for example impedance calibrations with adjustments for impedance unrelated to that of the body. Mapping of electrical activation time using a single electrode was, furthermore, a lengthy procedure, generally performed under fluoroscopic imaging, and thereby exposing the patient to undesirable ionizing radiation. Furthermore, in an arrhythmic heart, activation times at a single location may change between consecutive beats.

Because of the drawbacks of single-electrode mapping, a number of inventors have taught the use of multiple electrodes to measure electrical potentials simultaneously at different locations in the endocardium, thereby allowing activation time to be mapped more rapidly and conveniently, as described.

A reentrant circuit that produces sinus PVC's is one pathological condition amenable to ablative treatment. Identifying the optimum point of line of ablation is a practical difficulty, even with modern electroanatomic mapping equipment. U.S. Pat. No. 7,245,962 to Ciaccio et al. proposes a method and system for identifying and localizing a reentrant circuit isthmus in a heart of a subject during sinus rhythm. The method may include (a) receiving electrogram signals from the heart during sinus rhythm via electrodes, (b) creating a map based on the electrogram signals, (c) determining, based on the map, a location of the reentrant circuit isthmus in the heart, and (d) displaying the location of the reentrant circuit isthmus.

U.S. Patent Application Publication No. 2009/0099468 to Thiagalingam et al. proposes locating a region of interest to ablate by recording electrogram data and corresponding spatial location data of an electrode that records the electrogram data; defining at least one reference channel containing a reference beat for determining temporal locations and against which beats of the recorded electrogram data are compared; examining the recorded electrogram data; defining a temporal location for each beat of the recorded electrogram data, and creating and analyzing an index of the temporal locations and other information of the beats within the recorded electrogram.

SUMMARY OF THE INVENTION

There is provided according to embodiments of the invention a method of ablation, which is carried out by inserting a probe into a heart of a living subject, urging the mapping electrode of the probe into a contacting relationship with a target tissue in a region of interest of the heart, and while detecting a cardiac arrhythmia, using the mapping electrode to associate a local activation time with a first location in the region of interest. The method is further carried out while detecting an absence of the cardiac arrhythmia and maintaining the contacting relationship, by associating the local activation time with a second location in the heart, assigning electrical data of the first location to the second location, and generating an electroanatomic map of the heart by including at least the second location for display thereof using the assigned electrical data of the first location.

According to an aspect of the method, detecting a cardiac arrhythmia and detecting an absence of the cardiac arrhythmia comprise obtaining electrocardiographic signals via the mapping electrode, holding a series of the electrocardiographic signals in a buffer, selecting a first signal from the buffer as indicative of the cardiac arrhythmia, and selecting a second signal from the buffer as indicative of the absence of the cardiac arrhythmia.

An additional aspect of the method includes navigating an ablation electrode to the assigned electrical data of the second location for ablation thereof referencing the electroanatomic map while navigating the ablation electrode.

Another aspect of the method includes displaying the first location on the electroanatomic map and excluding the first location from computations in generating the electroanatomic map.

According to one aspect of the method, detecting a cardiac arrhythmia includes identifying premature ventricular contractions wherein a cycle length thereof is within a predetermined range.

In a further aspect of the method, the probe has multiple mapping electrodes and the method is carried out by acquiring multiple instances of the first location and the second location using respective ones of the mapping electrodes.

Yet another aspect of the method is carried out by pace mapping and determining at respective locations a pace map correlation between signals produced during ventricular tachycardia and signals produced by pace mapping and wherein assigning electrical data includes assigning the pace map correlation of the first location to the second location.

There is further provided according to embodiments of the invention a medical apparatus, including a probe, adapted for insertion into a heart, the probe including an elongated body, and a mapping electrode disposed on a distal portion of the body, a memory having programs stored therein, a display, and a processor linked to the display that is coupled to access the memory to execute the programs. The processor is connectable to receive an input provided by the mapping electrode, wherein the programs cause the processor to perform the steps of obtaining electrocardiographic signals from a target in the heart via the mapping electrode, holding a series of the electrocardiographic signals in a buffer, selecting a first signal from the buffer as indicative of a cardiac arrhythmia, the first signal occurring at a first point in time, and selecting a second signal from the buffer as indicative of an absence of the cardiac arrhythmia, the second signal occurring at a second point in time, associating a first local activation time of the target at a first location of the mapping electrode at the first point in time, associating a second local activation time of the target at a second location of the mapping electrode at the second point in time, assigning electrical data of the first location to the second location, generating an electroanatomic map based on the assigned electrical data at the second location, and presenting the electroanatomic map on the display, the electroanatomic map showing the first location and the second location.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

Definitions

The term "physical coordinates" of a point refers to coordinates of a point in the body of the subject that are determined with respect to fiducials or natural anatomic landmarks.

The term "map coordinates" of a point as used herein refers to coordinates or a point relative to a reference point on an electroanatomic map.

System Description

Figure 1:
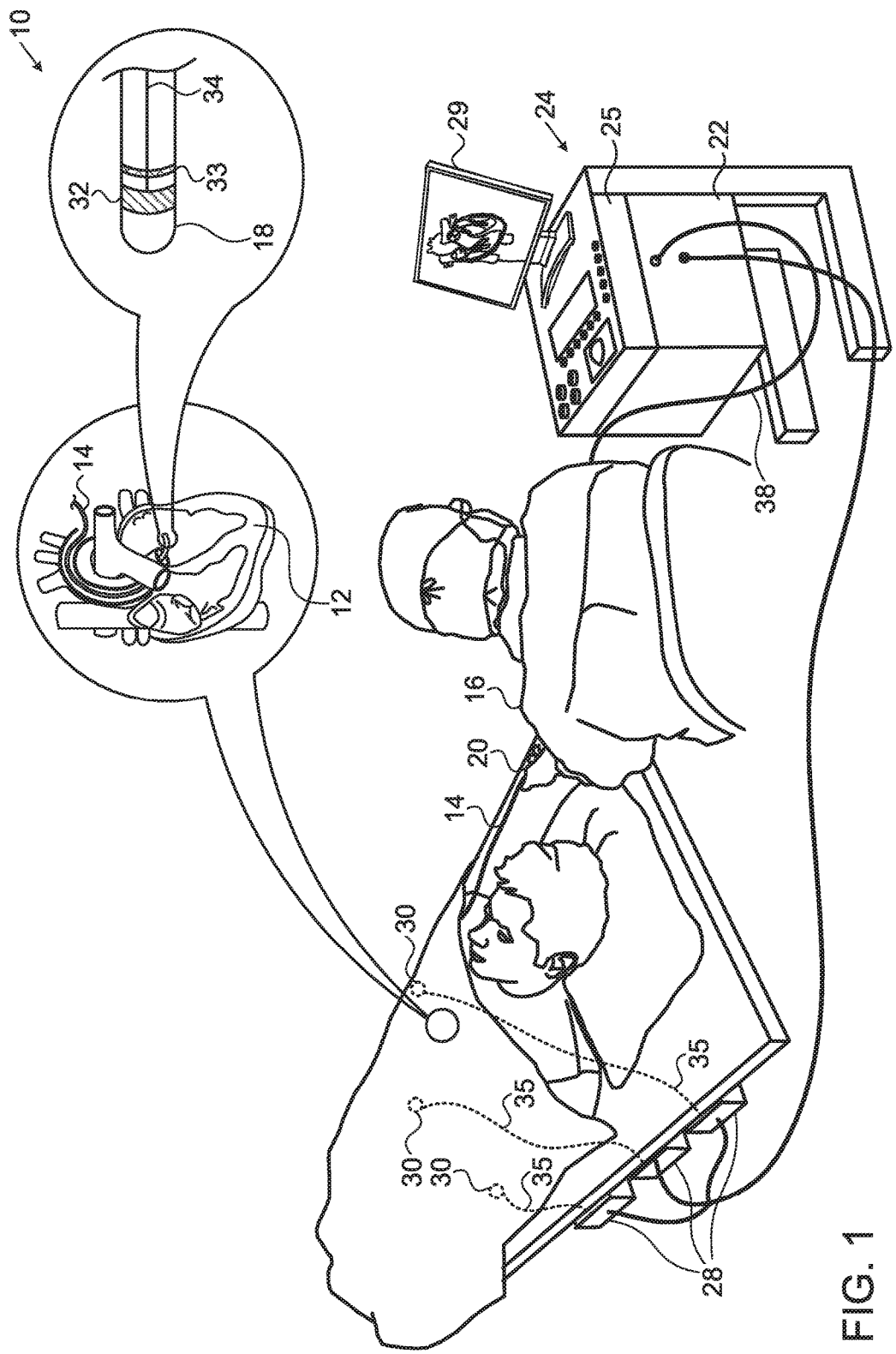
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, Electrical activation maps, such as local activation time maps, may then be prepared, according to the methods disclosed in U.S. Pat. Nos. 6,226,542, and 6,301, 496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14, and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Application of the system 10 to the ablation of regions causing transient arrhythmias, e.g., short runs of PVC's, presents certain technical difficulties. The medical procedure encompasses two stages, which may be accomplished in the same or different sessions.

In any case, in a first stage, one object is to identify a point having the shortest local activation time in an arrhythmogenic region of the heart, referred to herein as a "PVC point". Typically, an electroanatomic map is generated during the first stage. Although aspects of the invention are described for convenience with respect to PVC's, its principles are equally applicable to premature atrial contractions.

In a second stage, which occurs subsequent to the first stage, ablation of tissue in a region about the PVC point is performed. This is intended to interrupt automatic focal electrical activity and thereby prevent recurrence of the arrhythmia. In the second stage, the ablation electrode is navigated to the PVC point, which is a location on the electroanatomic map having the previously determined shortest local activation time. Often, by the time ablation has been accomplished, the patient has returned to sinus rhythm (SR). The term "sinus rhythm" is employed herein for convenience as an example of a stable cardiac rhythm. It will be recalled that in the case of a patient with infrequent premature ventricular contractions, the abnormal heart rate originating from the ventricle appears infrequently and in short bursts (1-3 beats). The heart is mostly in sinus rhythm, except that from time to time short PVC bursts appear. When creating a map consisting of PVC location points and their associated activation times, a discrepancy likely exists between the locations of the map's points (PVC geometry) and the navigational catheter, as the ablation catheter location is displayed mostly in sinus rhythm. As a result, the ablated area will not be optimum to correct the patient's arrhythmia. It is believed that the geometry of the heart differs during sinus rhythm, compared to its geometry during runs of ventricular tachycardia. In any event, it is desirable to accurately identify the physical location of the PVC point subsequent to its original determination.

In embodiments of the invention, the following procedure is suitable for recording signals during mapping: record approximately 2.5 seconds of each mapping electrode, and capture PVC complexes in a beat buffer, which holds and graphically displays the last few beats recorded by the electrocardiogram. Typically, 10 beats are held in the beat buffer. Inspection of the beat buffer allows abnormal beats such as PVCs to be identified automatically or automatically with operator assistance, or manually by the operator. This phase may be automated according to an operator-selected cycle length range, a procedure, which is available in the above-noted CARTO system. Alternatively, the operator can manually acquire a point and the related beat buffer whenever he notices a PVC occurrence.

Operation

Figure 2:
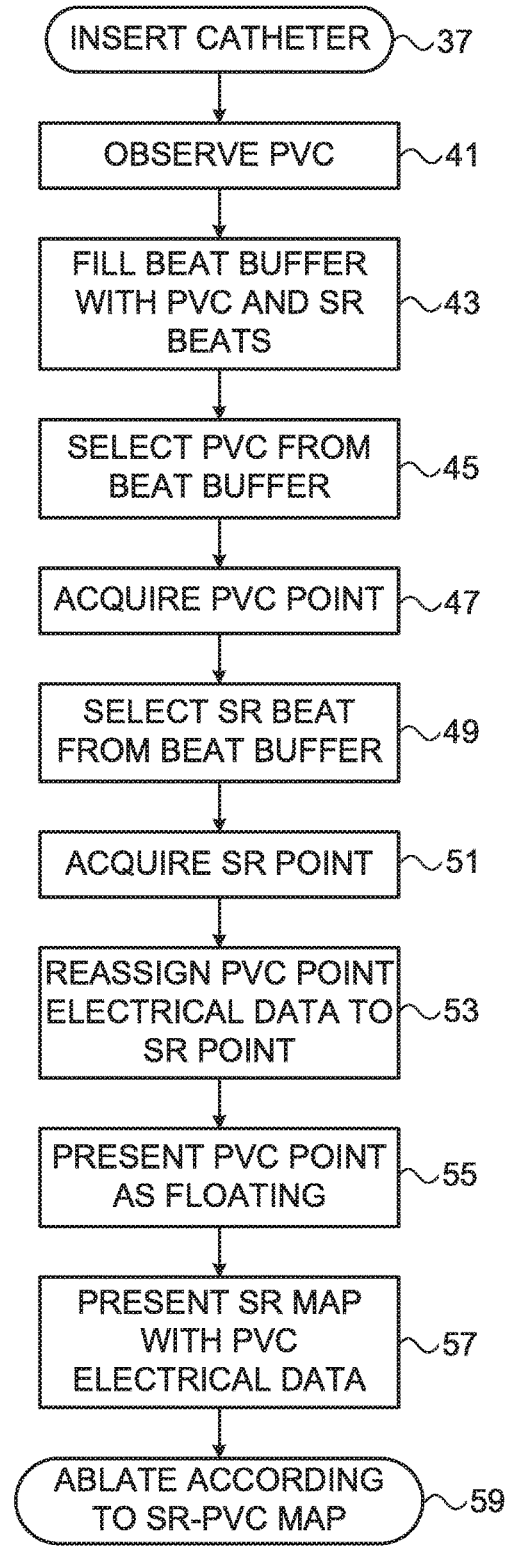
FIG. 2 is a flow chart of a method of mapping arrhythmogenic areas producing ventricular premature beats in accordance with an embodiment of the invention.

Reference is now made to FIG. 2, which is a flow chart of a method of mapping arrhythmogenic areas producing ventricular premature beats while the subject is in sinus rhythm, in accordance with an embodiment of the invention. The figures described below are obtained using the CARTO 3 system, and are presented for convenience. However, the method may be performed with other imaging and mapping systems.

Figure 3:
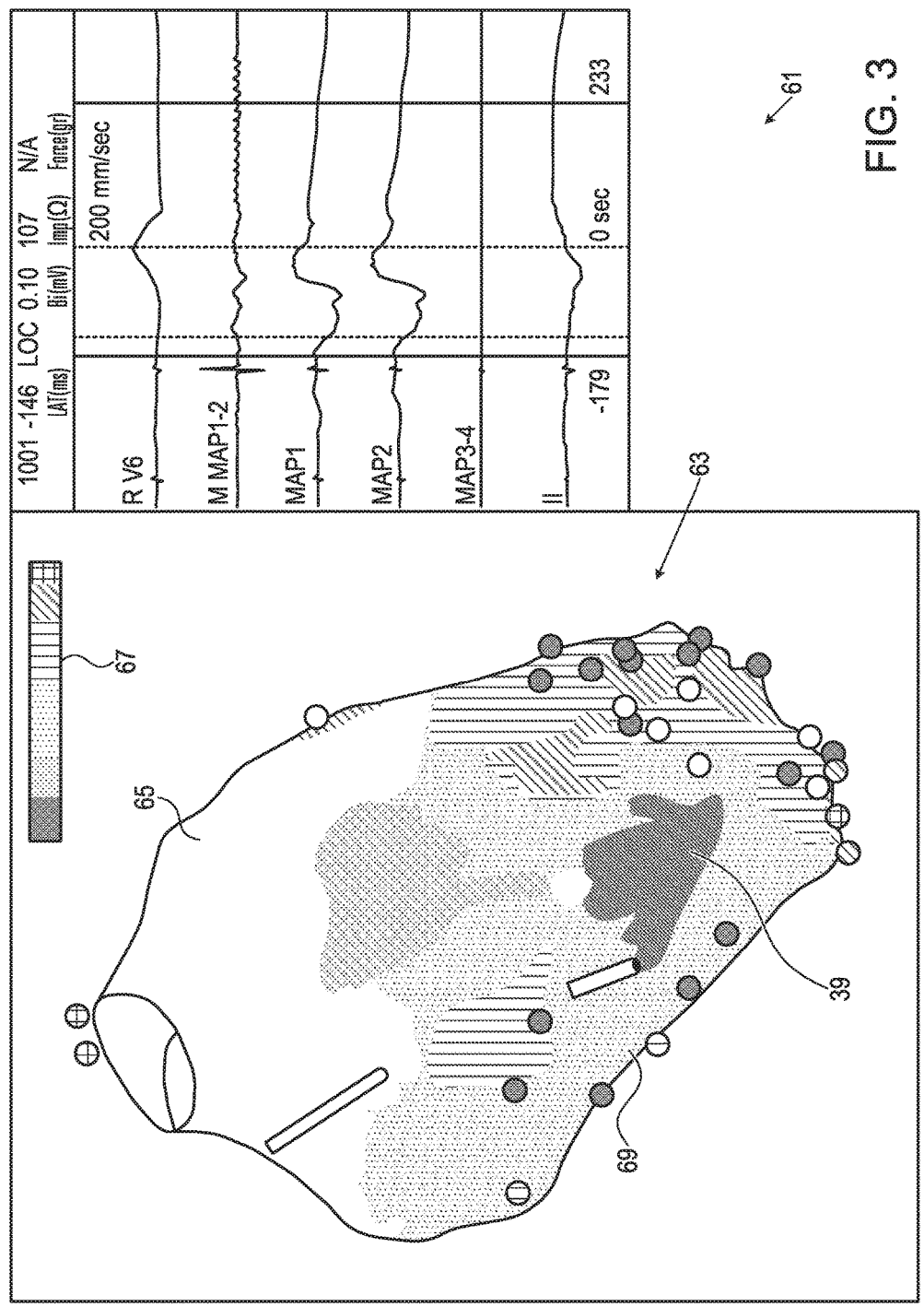
FIG. 3 is a screen display illustrating a representative local activation time map of a heart in accordance with an embodiment of the invention.

At initial step 37, a cardiac catheter having mapping electrodes and location sensors is inserted into the heart of a subject, using known methods. Catheters such as the PentaRay® NAV or Navistar® Thermocool® catheters, available from Biosense Webster, are suitable for use in initial step 37. The catheter is navigated to an abnormal area 39 (FIG. 3).

It is assumed that the subject is experiencing transient PVCs, either spontaneously occurring, or induced as noted above. The appearance of a PVC is noted at step 41.

Next, at step 43, the beat buffer is filled with PVC and SR beats, and frozen to prevent its replacement by new beats.

The method continues with step 45. A beat showing a qualifying electrical abnormality, e.g., a PVC, is identified on the beat buffer. This step may be performed automatically or by the operator. Next, at step 47, a point in the area 39, referred to for convenience as a "PVC point" is automatically acquired based on the beat in the beat buffer that was chosen in step 45. Optionally, the PVC point is acquired only if the cycle length of the selected beat falls within a predetermined range. Acquisition of the point comprises (1) determining the location the point, typically by using a location sensor to determine the position of the mapping electrode; (2) obtaining electrical data regarding the point from the mapping electrode, specifically its LAT; and (3) displaying the point on a map, e.g., an LAT map.

When catheters having multiple mapping electrodes are used, e.g., spline or lasso catheters, many points may be acquired concurrently. The PVC point ideally has the earliest local activation time within the abnormal area; however this is not essential; points throughout the area 39 (FIG. 3) may be acquired and displayed.

Next, at step 49, a second beat (SR beat) is selected from the beat buffer. The second beat represents normal sinus rhythm for the patient. Then, at step 51, a second point (SR point) is acquired and displayed on the same map as the PVC point. Generally, the locations of the PVC point and the SR point differ on the map, as explained above.

Next, at step 53, electrical information, e.g., the local activation time (LAT) of the PVC point that was established in step 47 is associated with the SR point in a single representative display by assigning the information to the SR point.

Next, at step 55, the PVC point is designated as "floating", meaning that the location of the PVC point may be indicated on LAT maps to indicate the disparity in the geometry of the heart when it is experiencing PVCs and SR. However, the PVC point is excluded from computations in the generation of such maps, and does not contribute to the map geometry and its electrical information. In consequence, a LAT map generated during sinus rhythm reflects the geometry of the heart in sinus rhythm, including the location of the SR point. However, the map is adjusted to associate the electrical information of the PVC point at the location of the SR point.

Then, at step 57, the LAT map is regenerated or adjusted to reflect the new data of the SR point. In other words, the SR map is presented with PVC electrical data. This version is referred to as a SR-PVC map. As explained above, the SR-PVC map reflects the geometry of the heart during sinus rhythm, but has the activation time of the heart while experiencing PVCs.

Steps 41-57 may be performed concurrently using different mapping electrodes, for example in a spline or lasso catheter. Additionally or alternatively steps 41-57 may be iterated to present multiple SR points having reassigned PVC data on the map.

The procedure ends at final step 59. If appropriate, ablation may be performed at the data-adjusted SR points with an ablation catheter displayed in SR locations. In such case, navigation of the ablation electrode may be guided by the SR-PVC map prepared in step 57.

EXAMPLES

Reference is now made to FIG. 3, which is a screen display 61 illustrating a representative local activation time map 63 of a heart 65 taken during performance of step 43, in accordance with an embodiment of the invention. The procedure for generating a local activation time map using a mapping catheter is known, and therefore its details are not discussed herein. Local activation times are typically coded using pseudocolor. In FIG. 3, local activation times information is coded using patterns in accordance with a key 67. These patterns simulate the pseudocolors of an actual functional map. The area 39 has a relatively short LAT, and may be automatically flagged or selected by an operator as abnormal. The area 39 is circumscribed by an area 69 that has a relatively longer local activation time.

Figure 4:
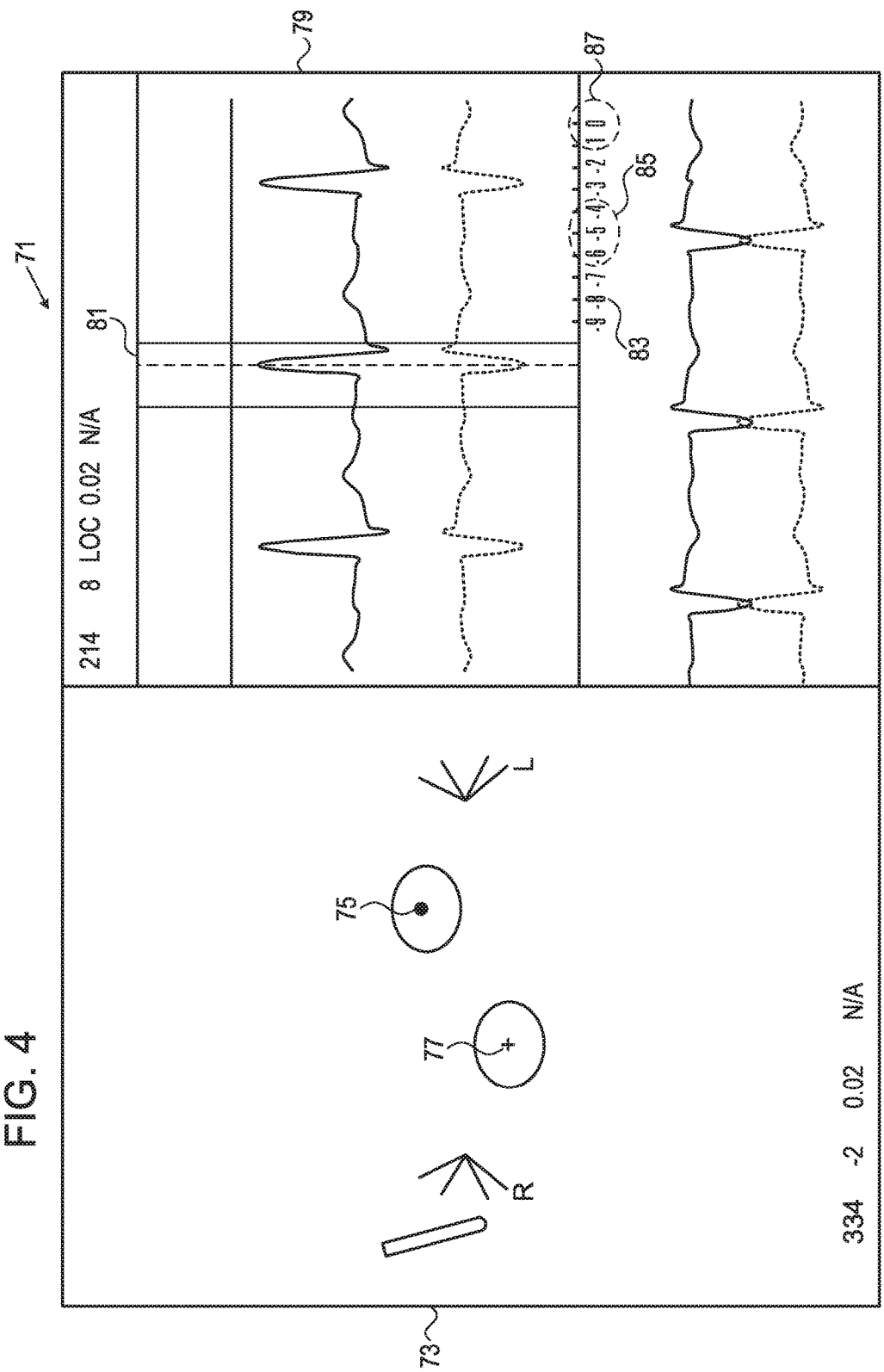
FIG. 4 is a screen display of a local activation time map 73 illustrating points of interest, in accordance with an embodiment of the invention.

Reference is now made to FIG. 4, which is a screen display 71 of a local activation time map 73 illustrating points of interest, in accordance with an embodiment of the invention. The map 73 shows the locations of PVC point 75 and SR point 77 that were obtained according to the procedure described above in reference to FIG. 2. The points 75, 77 are enclosed by circles for improved visibility. The beats selected from the beat buffer in order to acquire the points 75, 77 are shown in right pane 79 with a window of interest interval 81. The right pane 79 also shows the activation times of the PVC point 75 and SR point 77 on a scale 83 in the lower right portion. The beats selected are the SR and PVC points indicated by circles 85, 87, respectively. In other words, isochronal points are acquired from an area of interest using the beat buffer during PVCs (step 45) and during sinus rhythm (step 49) are shown on the map 73 as the points 75, 77 respectively. The points 75, 77 were measured at different times, based on different beats in the beat buffer, and thus are associated with different time stamps. It is evident that they have different map locations. In particular, the LAT map displays the physical coordinates of an SR point whose associated activation time data was obtained at a different time.

Figure 5:
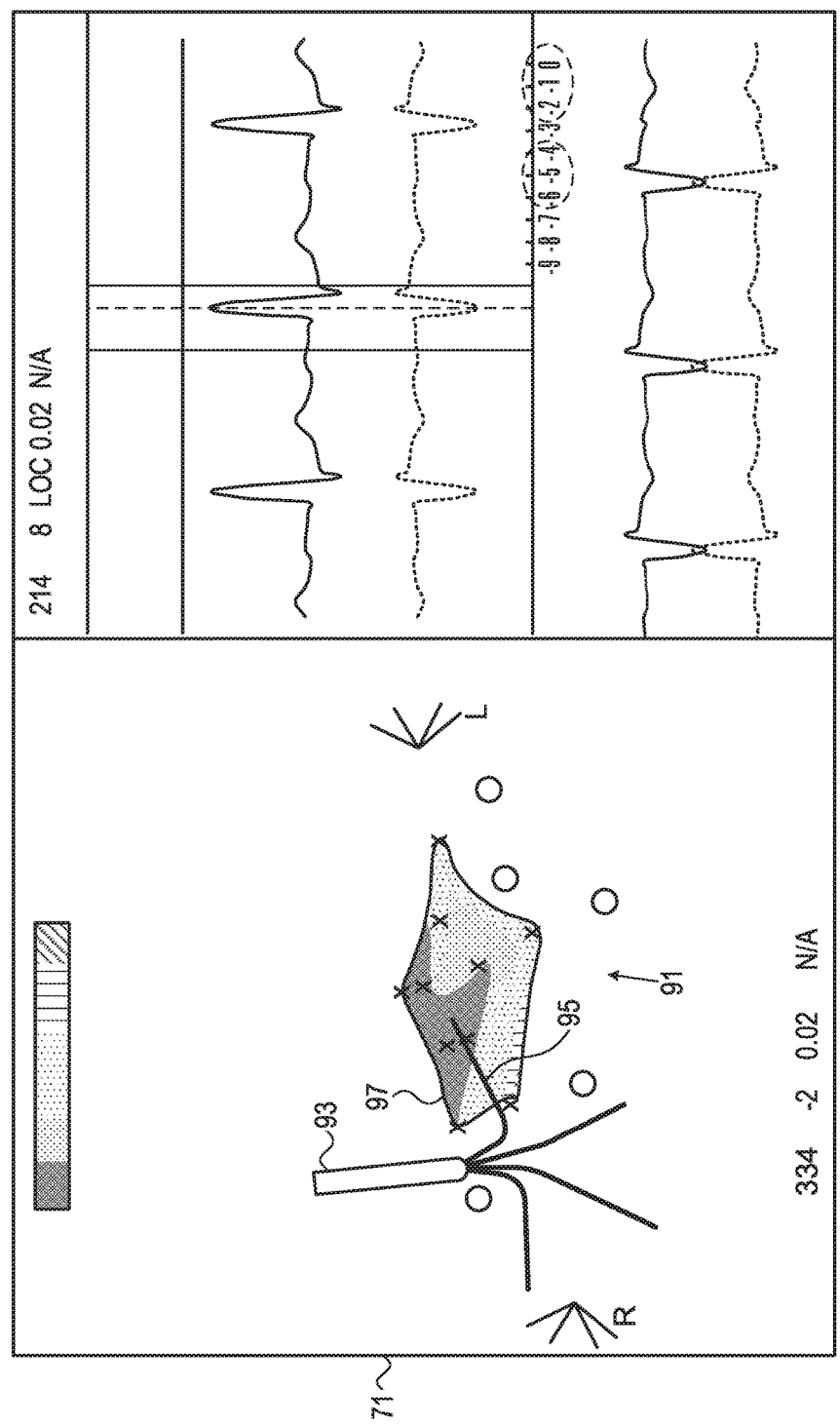
FIG. 5 is a screen display illustrating a role of a spline catheter in the generation of a local activation time map in accordance with an embodiment of the invention.

Reference is now made to FIG. 5, which is a screen display 89 illustrating a role of a spline catheter in the generation of a local activation time map 91, in accordance with an embodiment of the invention.

A spline catheter 93, e.g., the above noted Pentaray NAV catheter has been navigated such that an electrode of one of the spline, spline 95 is in contact with a point on a colored area 97, which has anomalous short activation times throughout. By appropriate repositioning of the spline catheter 93, PVC and SR points may then be automatically acquired using one or more splines, and processed according to the method described above with reference to FIG. 2.

Alternate Embodiment

Another embodiment of the invention involves pace mapping, for example using PaSo™ software.

Pace mapping is a diagnostic technique used for identification of ventricular tachycardia foci. This involves pacing the chamber at the ventricular tachycardia rate, then comparing a body surface 12-lead ECG acquired during pacing to an ECG recorded during clinical arrhythmia, either induced or previously recorded.

In this embodiment, the mapping phase is used to identify a pace-map correlation, i.e., a correlation between signals produced during ventricular tachycardia and signals produced by pace mapping, referred to as pace mapped— induced signal (PM-IS) correlation, as taught in commonly assigned U.S. Pat. No. 7,907,994 to Stolarski et al., which is herein incorporated by reference. A paced rhythm point serves as the PVC point from which PVC's originate. A map produced during pacing functions in the same manner as the map produced during sinus rhythm in the previous embodiment.

Figure 6:
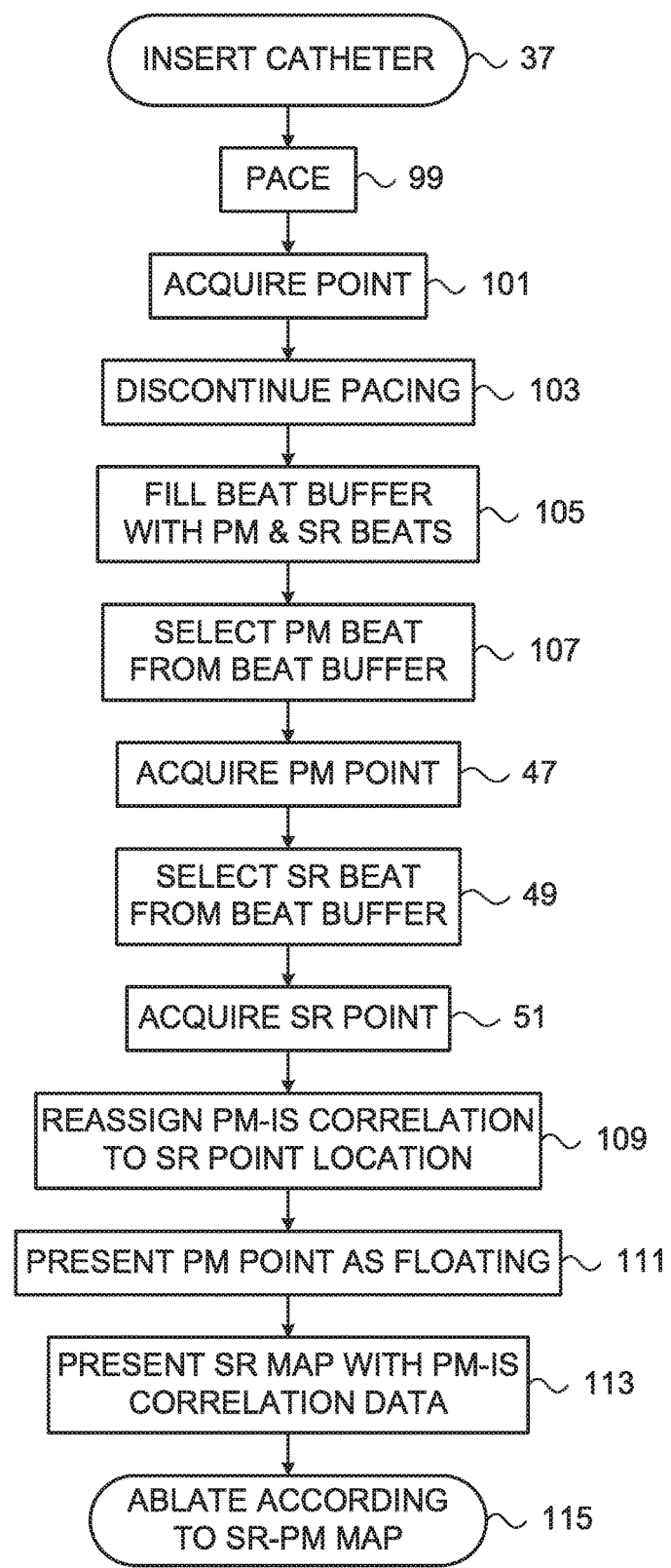
FIG. 6 is a flow chart of a method of mapping arrhythmogenic areas producing ventricular premature beats in accordance with an alternate embodiment of the invention.

Reference is now made to FIG. 6, which is a flow chart of a method of mapping arrhythmogenic areas producing ventricular premature beats while the subject is in sinus rhythm, in accordance with the preceding alternate embodiment of the invention. Some of the steps in FIG. 6 are performed in the same manner as those of FIG. 2. Their description is not repeated in the interest of brevity.

After performing initial step 37, pacing is conducted at step 99. A point is then acquired at step 101, and pacing is then discontinued at step 103.

Next, at step 105, the beat buffer is filled with pace-mapped (PM) beats and SR beats.

Next, at step 107, a PM beat is selected from the beat buffer.

Then, after performing steps 47, 49 and 51 as described above, at step 109, the pace-mapped correlation based on the PM point acquired in step 47 is assigned to the SR point location that was selected in step 51.

Next, at step 111, the PM point is presented as floating.

Next, at step 113, the SR Map is presented with PM-IS correlation data, referred to as a SR-PM map.

Then, at final step 115, ablation is performed according to the SR-PM map.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of mapping, comprising the steps of:
inserting a probe into a heart of a living subject, the probe having a mapping electrode;
urging the mapping electrode into a contacting relationship with a target tissue in a region of interest of the heart;
providing a memory having programs stored therein;
providing a display; and
providing a processor linked to the display and being coupled to access the memory to execute the programs, the processor being connectable to receive an input provided by the mapping electrode, wherein the programs cause the processor to perform the steps of:
obtaining electrocardiographic signals from a target in the heart via the mapping electrode;
holding a series of the electrocardiographic signals in a beat buffer;
freezing the beat buffer to prevent replacement by new beats;
identifying a beat in the beat buffer indicating a PVC (premature ventricular contraction), said beat being a PVC beat,
acquiring a PVC point based on the PVC beat, said PVC point only being acquired if the cycle length of the PVC beat falls within a predetermined range;
identifying an SR (sinus rhythm) beat from the beat buffer, said SR beat representing normal sinus rhythm;
acquiring an SR point based on said SR beat;
displaying the PVC point and the SR point on a single electroanatomic map;
associating the local activation time (LAT) of the PVC point with the SR point in a single representative display, said association being accomplished by assigning the LAT of the PVC to the SR point; and
generating a further electroanatomic map, said further electroanatomic map being an SR-PVC map, said SP-PVC map reflecting the assignment of the LAT of the PVC to the SR point, said SR-PVC map reflecting a geometry of the heart during sinus rhythm, while reflecting activation time of the heart while experiencing PVC,
whereby ablation may be performed at data-adjusted SR points with an ablation catheter displayed in SR locations, wherein navigation of an ablation electrode may be guided by the SR-PVC map.

2. The method according to claim 1, wherein the probe is a spline catheter having multiple mapping electrodes, and the processor is operative to acquire multiple instances of the first location and the second location using respective ones of the mapping electrodes.

3. The method according to claim 1, wherein the processor is operative for determining at respective locations a pace map correlation between signals produced during ventricular tachycardia and signals produced by pace mapping and wherein assigning electrical data comprises assigning the pace map correlation of the first location to the second location.

* * * * *